(12) United States Patent
Qureshi et al.

(10) Patent No.: US 8,290,229 B2
(45) Date of Patent: Oct. 16, 2012

(54) SYSTEM AND METHOD FOR COUNTING FOLLICULAR UNITS

(75) Inventors: Shehrzad A. Qureshi, Palo Alto, CA (US); Mohan Bodduluri, Palo Alto, CA (US)

(73) Assignee: Restoration Robotics, Inc., San Jose, CA (US)

( * ) Notice: Subject to any disclaimer, the term of this patent is extended or adjusted under 35 U.S.C. 154(b) by 0 days.

(21) Appl. No.: 13/472,631

(22) Filed: May 16, 2012

(65) Prior Publication Data

US 2012/0230561 A1  Sep. 13, 2012

Related U.S. Application Data

(63) Continuation of application No. 12/162,604, filed as application No. PCT/US2007/076728 on Aug. 24, 2007, now Pat. No. 8,199,983.

(51) Int. Cl.
  *G06K 9/00* (2006.01)
(52) U.S. Cl. ....................................... 382/128
(58) Field of Classification Search ............... 382/128
  See application file for complete search history.

(56) References Cited

U.S. PATENT DOCUMENTS

| | | | |
|---|---|---|---|
| 4,807,163 A * | 2/1989 | Gibbons | ............... 702/19 |
| 5,331,472 A | 7/1994 | Rassman | |
| 5,524,069 A | 6/1996 | Inoue | |
| 5,782,851 A | 7/1998 | Rassman | |
| 5,873,888 A | 2/1999 | Costanzo | |
| 5,895,403 A | 4/1999 | Collinworth | |
| 6,585,746 B2 | 7/2003 | Gildenberg | |
| 6,949,115 B2 | 9/2005 | Mascio | |
| 6,973,931 B1 * | 12/2005 | King | ............... 132/212 |
| 6,993,168 B2 | 1/2006 | Loussouarn et al. | |
| 7,094,569 B2 | 8/2006 | Kim et al. | |
| 7,127,081 B1 | 10/2006 | Erdem | |
| 7,217,266 B2 | 5/2007 | Anderson et al. | |
| 7,277,120 B2 | 10/2007 | Gere et al. | |
| 7,335,641 B2 | 2/2008 | Kim et al. | |
| 7,477,782 B2 | 1/2009 | Qureshi et al. | |
| 7,627,157 B2 | 12/2009 | Qureshi et al. | |

(Continued)

FOREIGN PATENT DOCUMENTS

KR  2004-0053337  6/2004

(Continued)

OTHER PUBLICATIONS

PCT International Search Report for PCT/US07/76726, Forms PCT/ISA/220 and 210, Applicant Restoration Robotics, Inc., dated Apr. 24, 2008, (5 pages).

(Continued)

*Primary Examiner* — Clayton E LaBalle
*Assistant Examiner* — Dennis Hancock
(74) *Attorney, Agent, or Firm* — Lena I. Vinitskaya (57) ABSTRACT

A system and method for counting follicular units using an automated system comprises acquiring an image of a body surface having skin and follicular units, filtering the image to remove skin components in the image, processing the resulted image to segment it, and filtering noise to eliminate all elements other than hair follicles of interest so that hair follicles in an area of interest can be counted. The system may comprise an image acquisition device and an image processor for performing the method. In another aspect, the system and method also classifies the follicular units based on the number of hairs in the follicular unit.

24 Claims, 6 Drawing Sheets

U.S. PATENT DOCUMENTS

| | | | |
|---|---|---|---|
| 2001/0015380 | A1 | 8/2001 | Good et al. |
| 2002/0081006 | A1 | 6/2002 | Rogers et al. |
| 2006/0089555 | A1* | 4/2006 | Gummer et al. ............ 600/476 |
| 2006/0127881 | A1 | 6/2006 | Wong et al. |
| 2007/0078466 | A1 | 4/2007 | Bodduluri et al. |
| 2007/0106306 | A1 | 5/2007 | Bodduluri et al. |
| 2008/0002809 | A1 | 1/2008 | Bodduluri |
| 2008/0004633 | A1 | 1/2008 | Arata et al. |
| 2008/0033455 | A1 | 2/2008 | Rassman et al. |
| 2008/0216334 | A1 | 9/2008 | Pak et al. |

FOREIGN PATENT DOCUMENTS

| | | |
|---|---|---|
| WO | 03-044737 | 5/2003 |

OTHER PUBLICATIONS

PCT Written Opinion of the International Searching Authority, for PCT/US07/76726, Forms PCT/ISA/237, Applicant Restoration Robotics, Inc., dated Apr. 24, 2008, (5 pages).

PCT International Search Report for PCT/US07/76728, Forms PCT/ISA/220 and 210, Applicant Restoration Robotics, Inc., dated Apr. 17, 2008, (4 pages).

PCT Written Opinion of the International Searching Authority, for PCT/US07/76728, Forms PCT/ISA/237, Applicant Restoration Robotics, Inc., dated Apr. 17, 2008, (8 pages).

Fisher, Robert, S. Perkins, A. Walker and E. Wolfart, "Gaussian Smoothing", retrieved on Feb. 26, 2008 from the Internet <URL: http://homepages.inf.ed.ac.uk/rbf/HIPR2/gsmooth.htm>, 2003, pp. 1 to 8, (8 pages).

Inaba, M. and Inaba, Y., "Androgenetic Alopecia, Modern Concepts of Pathogenesis and Treatment", 29. Operative Treatment for Androgenetic Alopecia, Springer, 1996, pp. 238-244, 309. (9 pages).

Canfield, Douglas, BS, "Photographic Documentation of Hair Growth in Androgenetic Alopecia", Dermatologic Clinics, vol. 14, No. 4, Oct. 1996, pp. 713-721.

Hoffmann, Rolf and Van Neste, Dominique. "Recent Findings with Computerized Methods for Scalp Hair Growth Measurements". JID Symposium Proceedings. 10:3 Dec. 2005. pp. 285-288.

Jimenez, Francisco, MD and Ruifernandez, J. M. PhD, Distribution of Human Hair in Follicular Units—A mathematical Model for Estimating the Donor Size in Follicular Unit Transplantation. Dermatol Surg 1999; 25: pp. 294-298.

Lyubovitsky J. G. and Krasieva T. B. "In situ multiphoton optical tomography of hair follicles in mice". Journal of Biomedical Optics, 12(4), 044003 (Jul./Aug. 2007). pp. 044003-1 to 044003-8.

Office Action mailed Mar. 17, 2009, in connection with U.S. Appl. No. 12/281,613, (16 pages).

Response to Office Action filed Jun. 11, 2009, in connection with U.S. Appl. No. 12/281,613, (9 pages).

Vella, F.; Castorina, A; Mancuso, M,; Messina, G.; "Robust Digital Image Stabilization Algorithm using Block Motion Vectors." Consumer Electronics, 2002 ICCE, 2002 Digest of Technical Papers, International Conference on Jun. 18-20, 2002. pp. 234-235 (2 pages).

Communication from Australian Patent Office, dated Mar. 18, 2010, in relation to commonly assigned Australian Patent Application No. 2007286606, which is an Australian National Stage filing of PCT/US2007/076728. Applicant Restoration Robotics, Inc. (2 pages).

Ramesh Jain, Rangachar Kasture, and Brian G. Schunck. "Machine Visioin", 1995. Cover Page, Publication Page, Chapters 4 and 5, McGraw-Hill, Inc. (68 pages).

Communication from China State Intellectual Property Office, dated Sep. 1, 2010, in relation to commonly assigned Chinese Patent Application No. 200780031059.5, which is a Chinese National Stage filing of PCT/US2007/076728, along with an English Translation thereof. Applicant Restoration Robotics, Inc. (6 pages).

Communication from Korean Intellectual Property Patent Office, dated Sep. 17, 2010, in relation to commonly assigned Korean Patent Application No. 10-2009-7003097, which is a Korean National Stage filing of PCT/US2007/076728, along with an English Translation thereof. Applicant Restoration Robotics, Inc. (10 pages).

Non-Final Office Action mailed Nov. 21, 2011, In relation to commonly assigned Canadian Patent Application No. 2,661,660 (4 pages).

Supplemental Search Report issued by the European Patent Office on Jul. 2, 2012, in relation to European Patent Application No. 07841322.6, which is a European National Stage filing of PCT/US2007/076728. Applicant, Restoration Robotics, Inc. (6 pages).

"Methods in Quantitative Image Analysis", Oberholzer M. et al., Histochemistry and Cell Biology, Springer, Berlin, DE, vol. 105, No. 5, May 1, 1996, pp. 333-335. (23 pages).

"TrichoScan: A Novel Tool for the Analysis of Hair Growth in Vivo", Rolf Hoffmann, Journal of Investigative Dermatology, Nature Publishing Group, GB, vol. 8, No. 1, Jun. 1, 2003, pp. 109-115 (7 pages).

* cited by examiner

SYSTEM AND METHOD FOR COUNTING FOLLICULAR UNITS

RELATED APPLICATION DATA

This application is a continuation application of U.S. patent application Ser. No. 12/162,604, filed Jul. 29, 2008, now U.S. Pat. No. 8,199,983 which is a U.S. National Stage filing under 35 U.S.C. §371 of International Application No. PCT/US2007/076728, filed Aug. 24, 2007, which claims priority to U.S. patent application Ser. No. 11/467,283, filed Aug. 25, 2006. Priority to the aforementioned applications is hereby expressly claimed in accordance with 35 U.S.C. §§119, 120, 365 and 371 and any other applicable statutes.

FIELD OF INVENTION

This invention relates generally to hair transplantation procedures and more particularly to a system and method for counting follicular units using digital imaging and processing techniques for use in hair transplantation procedures.

BACKGROUND

Hair transplantation procedures are well-known, and typically involve (in a patient having male pattern baldness) harvesting donor hair grafts from the side and back fringe areas (donor areas) of the patient's scalp, and implanting them in a bald area (recipient area). Historically, the harvested grafts were relatively large (3-5 mm), although more recently, the donor grafts may be single follicular units. In particular, "follicular units" (also referred to herein as FU or FUs) are naturally occurring aggregates of 1-3 (and much less commonly, 4-5) closely spaced hair follicles that are distributed randomly over the surface of the scalp.

Figure 1:
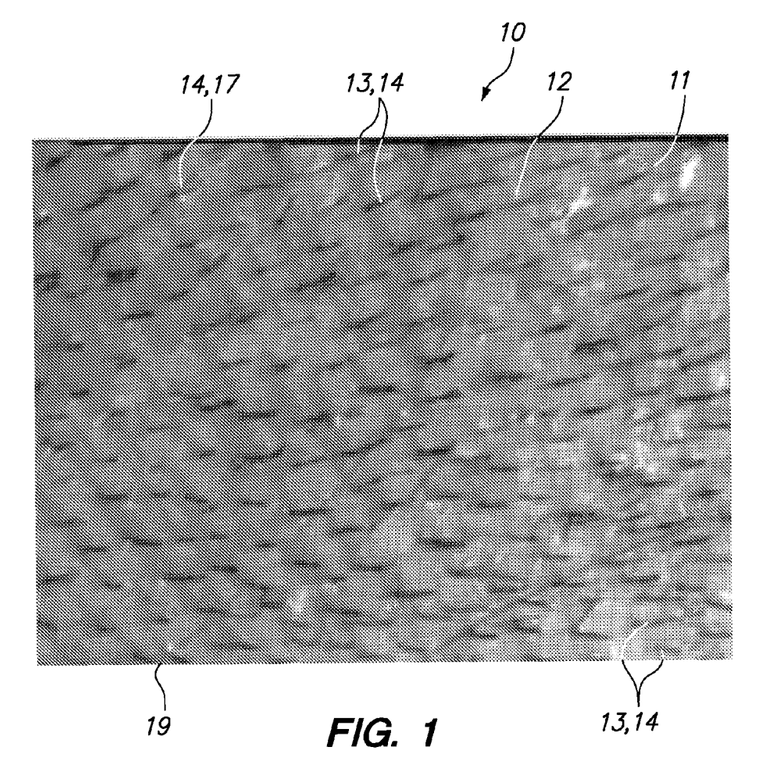
FIG. 1 is a print of a digital image of an exemplary section of a human scalp having a plurality of follicular units.

The follicular units may be classified, or "typed," based on the number of hairs in the unit and identified in shorthand as an "F1" for a single hair follicular unit, an "F2" for a two hair follicular unit and so on for follicular units with 3-5 hairs. In some cases of multiple hair follicular units, the hairs may appear to emanate from a single follicle or point in the skin. In other cases, the hairs may exit the skin surface at slightly spaced apart positions, but converge into a single follicular unit beneath the skin. Referring to FIG. 1, a print of a digital image of an exemplary section of a human scalp 11 having a variety of types of follicular units is shown. For example, the follicular unit 17 has two hairs and is therefore an F2, while follicular unit 13 is an F1 since it has only a single hair.

There are several reasons it is important and desirable to count and classify follicular units in a region of interest on a body surface. For one, the number of follicular units can be used in the planning process for a transplantation procedure. For instance, if this number sets the limit on the number of follicular units in that area that can be harvested for transplantation. However, in many cases, the doctor may want to implant only a certain percentage of the follicular units available, thereby leaving some coverage in the area being harvested. In addition, in many hair restoration transplant procedures, certain classes of follicular units are preferred.

As for classification, there are several reasons it is important and desirable to identify and classify follicular units based on the number of hairs in the follicular unit. It may be desirable to utilize a variety of classes (also referred to as "types") of follicular units to provide the desired attributes for the appearance of the transplanted hair. Such attributes can include the density of hair, the direction or orientation of hair, the particular mix of types of follicular units, and/or the appearance of randomness, among other possible attributes. An example of the use of various types of follicular units is as follows. It is preferable to transplant certain classes of follicular units into specific regions of the scalp. For example, single hair follicular units (F1s) are commonly implanted along the hairline that frames the face. Follicular units with more than one hair (F2s, F3s, etc.) are commonly implanted in the mid-scalp and crown. This arrangement of follicular unit distribution is thought to produce a more natural appearing aesthetic result.

Various procedures for hair transplantation have been previously disclosed, including both manual and mechanized to certain degrees of automation. In one well-known manual process, a linear portion of the scalp is removed from a donor area by dissection with a scalpel down into the fatty subcutaneous tissue. The strip is dissected (under a microscope) into the component follicular units, which are then implanted into a recipient area in respective puncture holes made by a needle. Forceps are typically used to grasp and place the follicular unit grafts into the needle puncture locations, although other instruments and methods are known for doing so.

In "Androgenetic Alopecia" (Springer 1996), M. Inaba & Y. Inaba disclose and describe a manual method for harvesting singular follicular units by positioning a hollow punch needle having a cutting edge and interior lumen with a diameter of 1 mm, which is about equal to the diameter of critical anatomical parts of a follicular unit. The needle punch is axially aligned with an axis of a follicular unit to be extracted and then advanced into the scalp to cut the scalp about the circumference of the selected follicular unit. Thereafter, the follicular units are easily removed, e.g., using forceps, for subsequent implantation into a recipient site with a specially devised insertion needle.

U.S. Pat. No. 6,585,746 discloses an automated hair transplantation system utilizing a robot, including a robotic arm and a hair follicle introducer associated with the robotic arm. A video system is used to produce a three-dimensional virtual image of the patient's scalp, which is used to plan the scalp locations that are to receive hair grafts implanted by the follicle introducer under the control of the robotic arm. The entire disclosure of U.S. Pat. No. 6,585,746 is incorporated herein by reference.

Automated systems and methods for transplanting are also disclosed in U.S. provisional patent application Ser. Nos. 60/722,521, filed Sep. 30, 2005, 60/753,602, filed Dec. 22, 2005, and 60/764,173, filed Jan. 31, 2006, and U.S. patent application Ser. Nos. 11/380,903, filed Apr. 28, 2006 (now published as US 2007/0078466) and 11/380,907, filed Apr. 28, 2006 (now published as US 2007/0106306). The foregoing applications are all hereby incorporated by reference into the present application in their entirety. For example, in U.S. patent application Ser. No. 11/380,907, referenced above, the disclosed system comprises a robotic arm having a harvesting and/or implantation tool mounted on the arm. One or more cameras are also mounted on the arm and are used to image the work space, such as a body surface. A processor is configured to receive and process images acquired by the cameras. A controller is operatively coupled to the processor and the robotic arm. The controller controls the movement of the robotic arm based, at least in part, on the processed images acquired by the cameras and the processor. The arm is controllably moveable to position the tool at a desired orientation and position relative to the body surface to perform transplantation of hairs.

In utilizing any of these systems and methods for hair transplantation, it is desirable to first plan the transplantation to select the follicular units to be harvested and transplanted and to determine the precise location where the hairs are to be implanted. Accordingly, in planning a hair transplantation procedure, specific follicular units from a specific location on a body surface may be selected for harvesting and transplantation into a different part of the body surface. The follicular units to be transplanted may be selected based on certain criteria, for example, the type of follicular unit (i.e. F1, F2, etc.), the orientation of the hair in the follicular unit, the density of the hair, etc. However, the process of counting, and characterizing each follicular unit can be tedious and time consuming. Therefore, there is a need for a system and method for counting and/or classifying follicular units using an automated system. A system and method for classifying follicular units is described in U.S. patent application Ser. No. 11/467,268, filed on or about Aug. 25, 2006, entitled SYSTEM AND METHOD FOR CLASSIFYING FOLLICULAR UNITS, the contents of which are incorporated by reference herein in its entirety.

SUMMARY

In accordance with a general aspect of the inventions disclosed herein, a system and method for counting follicular units using an automated system is provided. The system and method of the present invention may be utilized with systems and methods for transplantation of hair follicular units on a body surface. The system and method of the present invention is especially useful when implemented on, or integrated with, an automated system for hair transplantation.

In one aspect of the present invention, the method of counting follicular units comprises acquiring an image of a body surface having skin and follicular units, filtering the image to remove background components (such as skin, and optionally, some other small background components) in the image, processing the resulted image to produce a segmented image, and filtering noise to remove objects that do not correspond to the follicular units of interest. As a result, the remaining follicular units of interest can be counted. In one preferred embodiment, the acquired image is a digital image, although it is not necessary and analog images may be used. The analog image may be converted into a digital image using techniques known to those of ordinary skill in the art. According to the present invention, the step of removing skin components (and/or other background components) in the acquired image may be accomplished without limitation by any appropriate techniques and methods.

In one exemplary embodiment, filtering to remove background components is accomplished using a background subtraction technique where the skin surface is the background. One of the exemplary background subtraction techniques includes subtracting a leveled image (or blurred version of the input image) from the input image. Others involve a variance filter, edge detection based techniques, or keying off skin tones using color data. In another exemplary embodiment the step of removing background (skin) components is accomplished using a band-pass filter. Processing the image to produce a segmented image may be accomplished by any well-known techniques. In one exemplary embodiment of the method of the present invention, the segmented image is a binary image; however, multi-modal images (e.g. skin, moles, blood and/or other features are represented by more than two different image codes) are also within the scope of the present invention. The segmented image is further subjected to noise filtering, as necessary, to remove everything but hair follicles of interest. Examples of the type of noise that needs to be filtered include, but are not limited to, image noise, dandruff, blood speckles, moles, long uncut hair, etc.

All noise filtering could be accomplished simultaneously, or it could be broken into several separate steps: for example, first "small noise" corresponding to the small objects (e.g. small dandruff) is filtered, and then "larger noise" corresponding to the larger objects (e.g. long hair, large speckles of blood) is filtered.

Filtering of this "small noise" by removing such objects from the segmented image is referred to as a morphological open operation, which is a standard image processing technique known by those of ordinary skill in the art. The rest of the noise filtering is then performed on the image resulting from the morphological open operation. The noise filtering removes objects which do not meet criteria corresponding to a follicular unit. For example, the area, location or orientation of an object in the image may be one whose area, location or orientation does not correspond to an actual follicular unit (it could be cut hair that happens to be remaining on the scalp, for example). Whether the characteristics of an image of an object corresponds to hair may be determined by statistical comparison to the global nature of the same characteristics for images of objects in the selected image which are known to be hair, or alternatively, the characteristics can be compared to predetermined criteria based on patient sampling or other data (e.g., if the patient parts the hair in a certain way we know that the hairs should mostly be pointing in a given direction).

Each of the objects remaining in the image after the noise filtering is counted as a follicular unit. Thus, the method may be used to count follicular units.

In another aspect of the method of counting follicular units, filtering to remove skin components of the image using a band-pass filter may comprise a first filtering step using a low-pass filter having a first kernel and a second filtering step using a low-pass filter having a second kernel. In another feature of the present invention, the low-pass kernels may be Gaussian kernels. Those of ordinary skill in the art are familiar with, and understand how to implement, such low-pass filters and Gaussian filters.

In yet another embodiment of the method of the present invention, the counting of follicular units may be refined by using, for example, multiple imaging. It may also include a method for tracking the FU of interest and aligning the system to obtain the image. In one exemplary embodiment, first and second cameras are used to provide stereo images. The stereo images may be used to track an FU of interest within the images of the first and second cameras to adjust for movement of the body surface and/or movement of the cameras. In addition, the first and second cameras are aligned with the general orientation of the hair of the FU, so that images obtained provide good quality data for performing the remaining steps of the method of the present invention. The stereo images or multiple images may also be used to compute coordinate positions of the hairs. Then, images having a computed coordinate position which is inconsistent with a hair on said body surface can also be filtered out. Alternatively, the system and method of the present invention can use multiple cameras (or other image acquisition devices) or only one camera to make multiple images from various angles, including panoramic images. Camera could be moved either manually or with the assistance of a robot if the system used is a robotic system. This optional count refining step could be used as needed.

In another embodiment of the present invention, the method of counting of follicular units may be used in conjunction with a method of classifying follicular units, such as the methods described in U.S. patent application Ser. No. 11/467,268. In this way the follicular units of interest may be both counted and classified. The method of classifying a follicular unit (FU), as described in the Ser. No. 11/467,268, comprises acquiring an image of a body surface in which there are follicular units (FU) and processing such image to produce a segmented image of the FU. In one preferred embodiment the segmented image is a binary image, but it could be a multi-modal image, as described above. From the segmented image of the FU, a contour around the outer perimeter of the hair(s) of the FU may be calculated. For example, for an F1, the contour would generally be a line or surface following the outer surface of the single hair. The segmented image also allows the calculation of an outline profile of the FU. The outline profile disregards concavities in the contour of the image.

The outline profile is then compared to the contour to determine the number of "defects" in the outline profile. A defect in the outline profile may be defined, for example, as each of the concavities in the outline profile which divert from the contour. In the F2 example, there is one defect in the outline profile represented by the concavity formed by the "V" shape. In an F3, the contour will be generally shaped like two Vs sharing a common vertex and with one line forming one side of both Vs. The outline profile of an F3 will also have a generally triangular shape (although it may be a wider triangle than an F2). Thus, an F3 will have two defects. Therefore, it can be seen that the number of defects has a direct relationship to the type of follicular unit. In this case, the number of hairs for the FU equals the number of defects minus one.

In one embodiment of the method of classifying follicular units, the outline profile may be determined by calculating a convex hull contour pursuant to well-known image processing techniques. Other appropriate techniques for determining the outline profile are also within the scope of the invention disclosed.

In another embodiment of the method of classifying follicular units, procedure is provided for tracking the FU of interest to adjust for relative movement between an image acquisition device and the FU. Multiple image acquisition devices, such as cameras, may be aligned to obtain an image. In one exemplary embodiment, first and second cameras provide stereo images. The stereo images may be used to track an FU of interest within the images of the first and second cameras to adjust for movement of the body surface and/or movement of the cameras. In addition, the first and second cameras are aligned with the general orientation of the hair of the FU. In this way, an image is obtained which provides good quality data for performing the remaining steps of the method of classifying the FU.

In addition, the method of classifying a follicular unit may also adjust for follicular units having hairs which converge below the surface of the skin. In such case, the image will contain an image of a hair which is not a contiguous part of the contour of the FU of interest. To account for this situation, it is determined whether the separate hair is within a maximum distance from the hair(s) defining the contiguous contour of the FU of interest. The maximum distance is set to be a distance in which what appears to be a hair from a separate FU is most likely a part of the same FU as the FU of interest. The classification of the FU of interest then takes into account any additional hair(s) which are within a maximum distance from the hair(s) of the FU of interest.

Furthermore, the method of classifying a follicular unit may also adjust for hair images which appear to be a single hair but are in actuality multiple hairs. Thus, determining the number of defects will not provide an accurate classification because the merged hairs will result in fewer defects in the outline profile (and therefore fewer hairs) than are actually present in the FU of interest. To account for this situation, the method determines the width (or caliber) of each object representing a hair in the FU of interest using the image. Then, it is determined whether the width of each object representing a hair exceeds a maximum expected width for a single hair and compares them. The step of classifying the FU may also be based on a result of the above comparison and determination whether the width of an object representing a hair exceeds the maximum expected width and by how much. For example, if the width is between 1½ and 2 times the expected width, then the step of classifying will approximate such object as being two hairs. A similar approximation can be done for 3, 4 or 5 hairs.

Where the method of counting FUs is used in conjunction with the method of classifying an FU, the method of counting may be performed before, after or simultaneously with the method of classifying.

In another aspect of the present invention, a system for counting (and in some embodiments, also classifying) follicular units is provided. In one exemplary embodiment of the present invention, the system for counting an FU using an automated system comprises an image acquisition device and an image processor. One example of the image acquisition device is one or more cameras, such as any commercially available cameras. Instead of a camera, it could be a video recording device (such as a camcorder) or any other image acquisition device. While stereo imaging devices work well with the present invention, it is not necessary to have stereo imaging. Similarly, while it is preferred that the image acquisition device be a digital device, it is not necessary. It could be, for example, an analog TV camera that acquires an initial image which may be then digitized for further use in the method of the present invention. The image processor may comprise any device programmed and configured to perform the method of counting (and, optionally classifying) an FU according to the present invention. One non-limiting example of a suitable image processor is any type of personal computer ("PC"). Alternatively, the image processor may comprise an Application Specific Integrated Circuit (ASIC) or Field Programmable Gate Array (FPGA).

According to another aspect of the present invention, the image processor is provided that is programmed and configured to perform the method of counting (and, optionally classifying) an FU according to the present invention. Any suitable image processor is within the scope of the present invention. In one exemplary embodiment, an image processor for counting follicular units is configured for receiving an image of a body surface comprising skin and follicular units, filtering the image to remove background components, processing the image to produce a segmented image, and performing noise filtering to remove objects that do not correspond to follicular units of interest. Such image processor according to the present invention could be used in conjunction with various systems for planning of hair treatments, for harvesting and/or implanting follicular units (manual, semi-automatic, automatic, or robotic), as well as with various systems for counting or classifying follicular units; alternatively, it could be incorporated in any of such systems.

A system for counting follicular units using an automated system may be used in conjunction with or may comprise any of the transplantation systems described in the background above. For instance, the system described in U.S. patent application Ser. No. 11/380,907 may be programmed and configured to perform the methods of counting follicular units according to the present invention. The cameras on the system can provide stereo digital images and the robotic arm can properly position and orient the cameras. The selection of a region of interest may be performed by an operator at the user interface of the system (such as a computer having a monitor and input devices) or it could be automated through programming of the computer and/or controller.

Accordingly, a system and method for counting (and in some embodiments, also classifying) follicular units is provided. Other and further embodiments, objects and advantages of the invention will become apparent from the following detailed description when read in view of the accompanying figures.

BRIEF DESCRIPTION OF THE DRAWINGS

The invention is illustrated by way of example and not limitation in the figures of the accompanying drawings, in which like references indicate similar elements, and in which.

DETAILED DESCRIPTION OF THE ILLUSTRATED EMBODIMENTS

Referring first to FIG. 1, the system and method for counting follicular units according to the present invention generally begins with acquiring an image 10 of a body surface 11 using any appropriate image acquisition device. In one exemplary embodiment, such image acquisition device is one or more digital cameras. Alternatively, any other suitable imaging device may be utilized. The image acquisition device may produce a digital image, such as that produced by a digital camera, or it may produce an analog image (which may or may not be converted to a digital image at any point in the process). Although in this description of an exemplary embodiment, the image 10 is a digital image taken by a digital camera, the present invention is not limited to digital images taken by digital cameras. Instead of a camera, it could be a video recording device (such as a camcorder) or any other image acquisition device. While stereo imaging devices are currently preferred, it is not necessary to have stereo imaging. Similarly, while it is preferred that the image acquisition device be a digital device, it is not necessary. It could be, for example, an analog TV camera that acquires an initial image which is then processed into a digital image for further use in the method of the present invention. The body surface 11 has skin 12 and a plurality of follicular units 14 each having one or more hairs 13 (only a few of the follicular units 14 and hairs 13 are labeled in the figures). The photo of FIG. 1 is an image of a section of human scalp 11, but it is understood that the body surface 11 could be any area of any body having hair. The digital image 10 shows a variety of types of follicular units 14 (FU) on the scalp 11.

The image 10 may be acquired using one or more cameras of an automated hair transplantation system, such as the cameras described in the hair transplantation system of U.S. patent application Ser. No. 11/380,907, which is incorporated by reference herein in its entirety. The image from just one of the cameras can be used to produce the digital image 10. Alternatively, the process for obtaining the digital image 10 may be acquired by a more involved process which aligns the camera(s) to improve the image used to count a follicular unit of interest. In this exemplary process, a first camera and a second camera are used. The cameras are arranged and configured to obtain stereo images of a body surface at which cameras are directed. The cameras are first positioned to be directed at the body surface in an area known to have hair. A first image is acquired from the first camera and a follicular unit (FU) of interest is selected from within the first image. A second image of about the same region of the body surface as the first camera (except from a slightly different angle as provided by stereo cameras) is acquired from the second camera and the same FU of interest is selected from within the second image. The FU of interest can be selected in the images by an operator of the system or automatically by the system using a selection algorithm. The transplantation system is now able to track the FU of interest within the first and second images from the first and second cameras. The tracking procedure can be used to adjust for movement of the body surface and movement of the cameras when they are aligned to acquire the image(s) used for counting the FU.

Next, the first and second cameras are moved and oriented to be aligned with the general orientation of the hair of the FU. As the cameras are moved, additional images may be acquired and processed by the system in order to track the FU of interest. By aligning the cameras with the hair of the FU, a better image for counting the FU can be acquired. With the cameras in the desired alignment, the cameras acquire the images to be used in the next steps of the method of counting follicular units. The above description is provided strictly by way of example and not limitation. It is possible to use various multiple image acquisition devices, such as multiple cameras, or a single camera to take multiple images, including panoramic images, at different angles to track the FU of interest. As was previously explained, the image acquisition device does not have to be a digital image acquisition device, and the images initially obtained do not need to be digital images. The movement of the camera could be controlled by a robotic system, or manually, depending on the kind of system used.

When the image 10 is acquired, a region of interest 19 could be the entire image 10 or a selected sub-area of the entire image 10. In the example described herein, the selected region of interest 19 is co-extensive with the image 10. However, the selected region of interest 19 can be any subset area of the image 10. The region of interest 19 may be selected by an operator or the selection may be automated by the system. This region of interest within the image may be called the selected image 19. Accordingly, further references to a region of interest 19 or selected image 19 may refer to the entire image 10, or to any sub-area which may be selected or simply an inherent result of the acquired image 10.

It has been determined that it is beneficial first to remove background components from the acquired image in order to improve the accuracy and efficiency in the overall process for counting follicular units of interest. Generally, such background components correspond to the skin. In addition to the skin, these background components may also include some additional small objects, for example, dandruff or small blood speckles. Accordingly, further references to the filtering or removal of the skin (or skin components) is not limited to the skin alone but rather may include some additional small background components or objects; and any such references should mean filtering or removal of the background components. Any suitable method(s) for filtering background components, such as the skin, from the image are within the scope of the present invention.

In one exemplary embodiment, filtering of the skin 12 is accomplished using a background subtraction technique where the skin surface is the background. One of the exemplary background subtraction techniques includes subtracting a leveled image (or blurred version of the input image) from the input image. A correction may be made for non-uniform illumination and skin tones simultaneously by subtracting a blurred version of the input image from the input image. The blurred image may be formed by computing the local means of the selected image 19 (input image). The local means are calculated efficiently by convolving the input image with a Gaussian kernel. This filtering procedure may be tuned for a particular patient, ambient lighting, or other clinical situation, by adjusting the characteristics of the Gaussian kernel employed during the blurring process. In summary, the background subtraction technique of the above-described example is as follows:

(1) Blurred Image=Input image convolved with Gaussian (note: Gaussian could be replaced by any other suitable kernel)

(2) Image without Background=(Input Image)−(Blurred Image)

Other exemplary background subtraction techniques that may be utilized in the present invention include a variance filter, edge detection based techniques, or keying off skin tones using color data.

Figure 2:
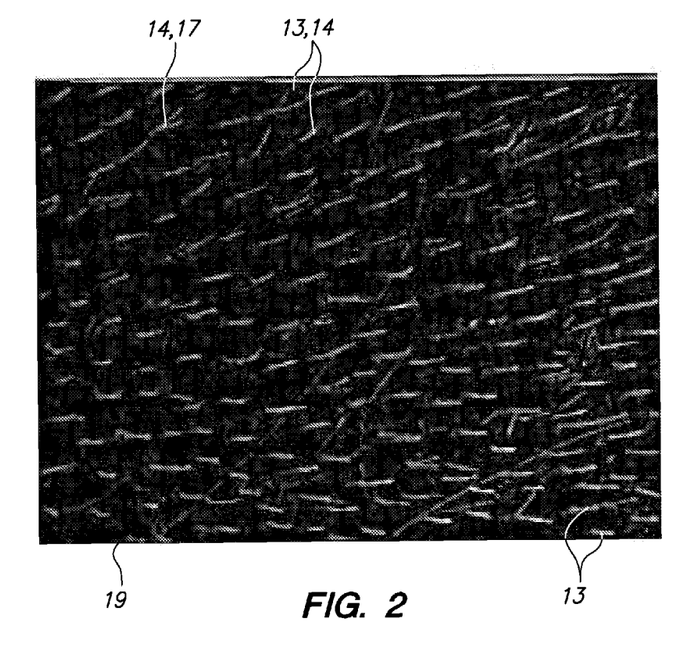
FIG. 2 is a print of the digital image of FIG. 1 after it has been filtered to remove skin components.

Another exemplary embodiment of the filtering step that may be used to filter the skin 12 from the selected image 19 is band-pass filtering. One exemplary approach is illustrated in FIG. 2 which shows a print of the digital image after the original selected image 19 has been filtered using a band-pass filter. The band-pass filter may comprise any suitable filter as known by those of ordinary skill in the art. The band-pass filtering can be accomplished by low-pass filtering the selected image twice and then subtracting the two resulting filtered images. The band-pass filter may comprise a first filtering step using a low-pass filter having a first kernel and a second filtering step using a low-pass filter having a second kernel. The first kernel is preferably different from the second kernel. In one embodiment of the present invention, the kernels of the low-pass filter(s) may be Gaussian kernels. The first Gaussian kernel may have substantially the following characteristics: support 21 pixels, sigma of 1.0. The second Gaussian kernel may have substantially the following characteristics: support 21 pixels, sigma of 0.075.

Figure 3:
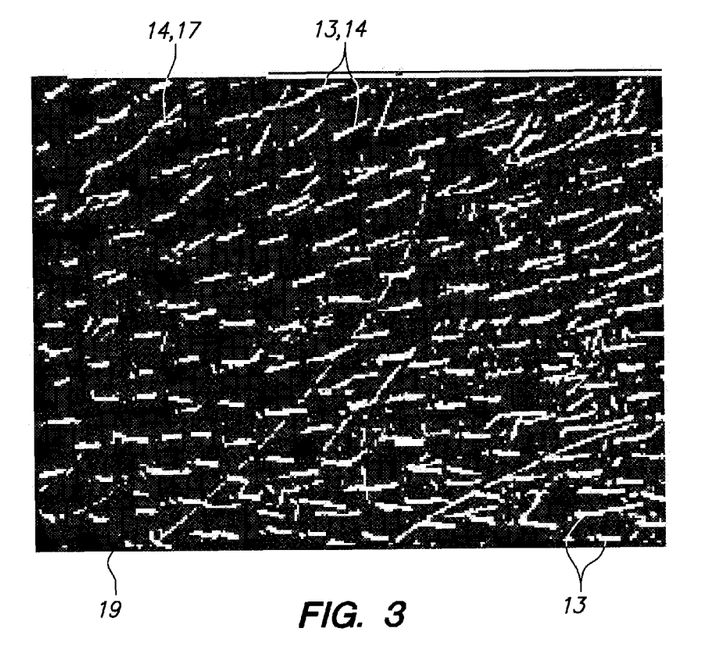
FIG. 3 is a print of the digital image of FIG. 2 after the image has been segmented.

Next, after removal of skin 12 (which may include removal of other small background components as mentioned above), the resulted image is processed using well-known image processing techniques to produce a segmented image. One example of a segmented image is a binary image. FIG. 3 is a print of the binary image after the image has been segmented. As discussed above, the segmented image is not limited to creating a binary image, but may also be multi-modal, i.e. differentiated into more than two different image codes corresponding to features such as moles, blood, hair and/or other features. The segmented image provides an improved and more clear image of the FU, however, it is still likely to contain certain "noise" that requires further filtering (e.g.: objects and artifacts that do not correspond to hair or specified hair). It was observed that removing background components, as described above, prior to obtaining the segmented image containing FU not only reduced the amount of the remaining noise in the segmented image, but also simplified and made more efficient the remaining steps of filtering all other objects that do not correspond to hair of interest.

Figure 4:
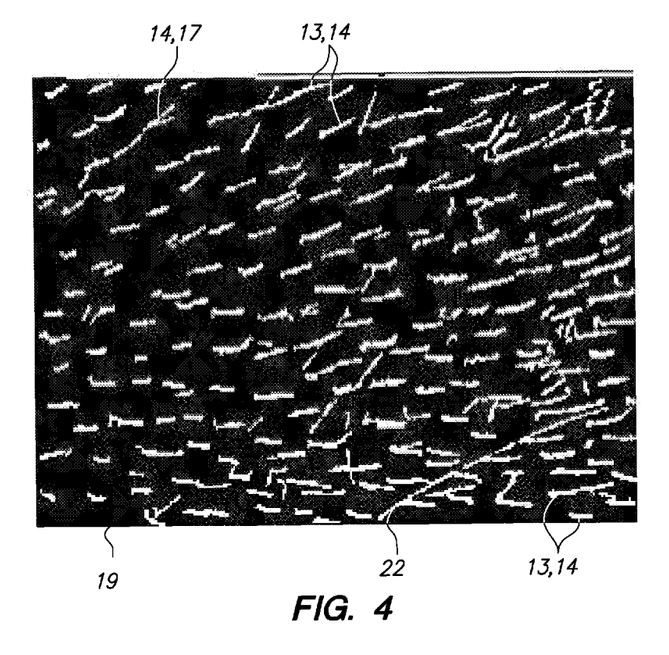
FIG. 4 is print of the digital image of FIG. 3 after a morphological open operation has been performed on the segmented image.

All noise still remaining in the segmented image could be filtered simultaneously, or it could be broken into several separate steps: for example, first "small noise" corresponding to the small objects (for example, some remaining smaller blood speckles, or remaining larger pieces of dandruff) may be filtered, and then "larger noise" corresponding to the larger objects (such as long uncut hair, or previously cut hair that still remains on the scalp) may be filtered, or visa versa. The example of the cut hair follicle that remains on the scalp and appears in the image would not be considered "an FU of interest," therefore; it needs to be filtered as noise. Filtering of the "small noise" from the segmented image is referred to here as a morphological open operation. A morphological open operation may be accomplished by using standard image processing technique known by those of ordinary skill in the art. FIG. 4 shows the resulting exemplary image after the morphological open operation. As can be seen in FIG. 4, the image may still contain some objects which do not correspond to the hair 13 of follicular unit 14. There are still objects which appear to be too long, too large, randomly oriented and/or in a location which probably does not contain hair.

Figure 5:
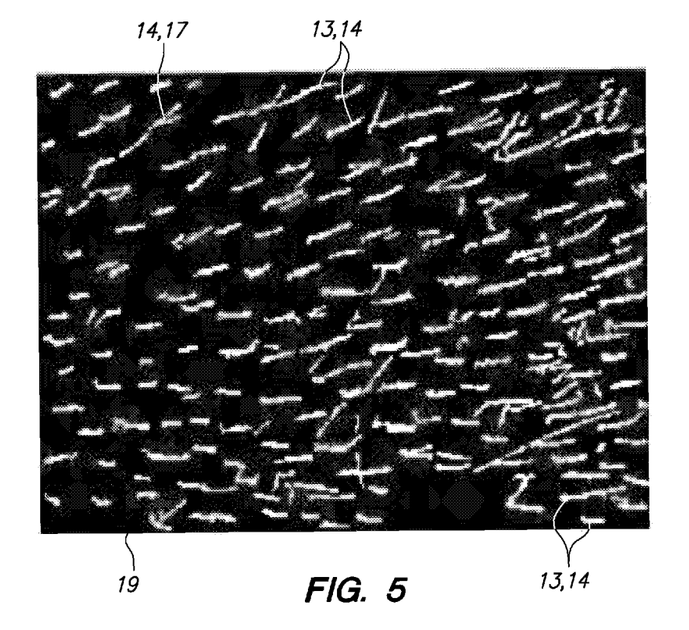
FIG. 5 is a print of the digital image of FIG. 4 after all noise filtering has been performed on the image.

Accordingly, additional noise filtering may be performed on the image resulting from the morphological open operation. The additional noise filtering removes larger objects which do not meet criteria corresponding to a follicular unit 14. Referring back to FIG. 4, the object 22 appears to be much longer and have a much larger area than the other objects in the image 19. Thus, it can be assumed that this object is probably not a hair 13 and therefore should be filtered out of the image. Turning now to the print of the image after the noise filtering step of FIG. 5, it can be seen that the object 22 has been filtered out of the image. The noise filtering step can filter based on a wide range of characteristics of the objects in the image, including without limitation, length, area, orientation and/or location. Whether the characteristics of an image of an object corresponds to hair may be determined by statistical comparison to the global nature of the same characteristics for images of objects in the selected image which are known to be hair, or alternatively, the characteristics can be compared to predetermined criteria based on patient sampling or other data. For instance, the noise filtering filter can be based on characteristics of a sampling of the other hairs on the body surface of the particular patient, or the characteristics of a sampling of hairs on a sample of patients, or on known predetermined data based on studies or research.

To summarize, all noise filtering from the segmented image could be accomplished simultaneously or in steps based on various criteria and as needed. Each of the objects remaining in the image after the noise filtering is counted as a follicular unit of interest. Thus, the method may be used to count follicular units.

Figure 6:
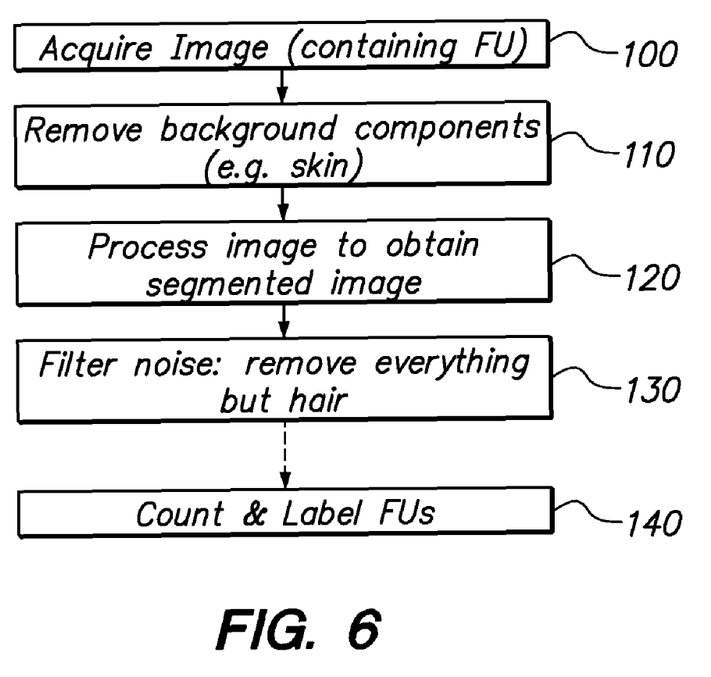
FIG. 6 is an exemplary flow chart of the method of counting of follicular units according to one exemplary embodiment of the present invention.

The basic steps of the above-described exemplary method of counting follicular units are summarized in the flow chart of FIG. 6. FIG. 6 is simply a flow chart representation of the method described above. At step 100, an image containing follicular units is acquired. At step 110, the acquired image is filtered to remove background components as explained above. At step 120, the image without background components is processed to produce a segmented image. At step 130, a noise filtering procedure is performed to remove artifacts and objects not corresponding to hairs of interest. As the result of the above steps, the number of remaining objects may be counted to determine the number of follicular units in the image (or a selected sub-area of the image). The FUs may also be labeled, if desired. FIG. 6 shows the additional counting and labeling steps 140.

In another embodiment of the present invention, the method of counting follicular units may be used in conjunction with a method of classifying follicular units, such as the methods described in U.S. patent application Ser. No. 11/467,268. In this way the follicular units of interest may be both counted and classified. The method of classifying a follicular unit (FU) comprises acquiring an image of a body surface in which there are follicular units (FU) and processing such image to produce a segmented image of the FU. In one preferred embodiment the segmented image is a binary image, but it could be a multi-modal image, as described above. From the segmented image of the FU, a contour around the outer perimeter of the hair(s) of the FU may be calculated. For example, for an F1, the contour would generally be a line or surface following the outer surface of the single hair. For a relatively straight hair, the contour would look like a rectangle. For an F2, the hairs typically form a "V" shape such that the contour looks like a block lettered "V".

The segmented image also allows the calculation of an outline profile of the FU. The outline profile disregards concavities in the contour of the image. For instance, for an F2, there is a concavity or "inwardly curved" portion in the contour formed by the descent in the contour from the one side of the top of the "V" to the vertex of the "V" and back up to the other side of the top of the "V". The calculated profile disregards this concavity such that the resulting outline profile looks like a triangle with one of the vertices of the triangle generally tracing the vertex of the "V" of the contour of the FU.

The outline profile is then compared to the contour to determine the number of "defects" in the outline profile. A defect in the outline profile may be defined, for example, as each of the concavities in the outline profile which divert from the contour. In the F2 example, there is one defect in the outline profile represented by the concavity formed by the "V" shape. In an F3, the contour will be generally shaped like two Vs sharing a common vertex and with one line forming one side of both Vs. The outline profile of an F3 will also have a generally triangular shape (although it may be a wider triangle than an F2). Thus, an F3 will have two defects. Therefore, it can be seen that the number of defects has a direct relationship to the type of follicular unit. In this case, the number of hairs for the FU equals the number of defects minus one.

In one non-limiting exemplary embodiment of the method of classifying follicular units, the outline profile may be determined by calculating a convex hull contour pursuant to well-known image processing techniques. Other appropriate techniques for determining the outline profile are also within the scope of the invention disclosed.

In another non-limiting exemplary embodiment of the method of classifying follicular units, procedure is provided for tracking the FU of interest to adjust for relative movement between an image acquisition device and the FU. Two or more cameras, or other image acquisition deices, could be aligned to obtain an image or multiple images. In one exemplary embodiment, stereo images may be used to track an FU of interest within the images of the first and second cameras to adjust for movement of the body surface and/or movement of the cameras. In addition, the first and second cameras are aligned with the general orientation of the hair of the FU. In this way, an image is obtained which provides good quality data for performing the remaining steps of the method of classifying the FU. The above description is provided by way of example and not limitation. Therefore, it is not necessary to use two cameras or stereo imaging, and the tracking procedure could be performed with multiple image acquisition devices, such as multiple cameras, as well as with a single camera that could take multiple images from various angles, including panoramic images. Camera may be moved either manually or with the assistance of a robot if the system used is a robotic system.

The method of classifying a follicular unit may also adjust for follicular units having hairs which converge below the surface of the skin. In such case, the image will contain an image of a hair which is not a contiguous part of the contour of the FU of interest. To account for this situation, it is determined whether the separate hair is within a maximum distance from the hair(s) defining the contiguous contour of the FU of interest. The maximum distance is set to be a distance in which what appears to be a hair from a separate FU is most likely a part of the same FU as the FU of interest. The classification of the FU of interest then takes into account any additional hair(s) which are within a maximum distance from the hair(s) of the FU of interest.

The method of classifying a follicular unit may also adjust for hair images which appear to be a single hair but are in actuality multiple hairs. If the image is taken at a certain angle to the hairs of an FU, the image of the hairs may merge and appear to be one hair. Thus, determining the number of defects will not provide an accurate classification because the merged hairs will result in fewer defects in the outline profile (and therefore fewer hairs) than are actually present in the FU of interest. To account for this situation, the method determines the width (or caliber) of each object representing a hair in the FU of interest using the image. Then, it is determined whether the width of each object representing a hair exceeds a maximum expected width for a single hair and comparing them. The step of classifying the FU then is also based on a determination whether the width of an object representing a hair exceeds the maximum expected width and by how much. For example, if the width is between 1½ and 2 times the expected width, then the step of classifying will approximate such object as being two hairs. A similar approximation can be done for 3, 4 or 5 hairs.

It should be understood that the method of counting FUs may be performed before, after or simultaneously with the method of classifying.

In yet another aspect of the present invention, a system for counting follicular units (and classifying FUs, as the case may be) is provided. As an exemplary embodiment, the system may comprise an image acquisition device and an image processor. Some non-limiting examples of an image acquisition device include one or more cameras, such as any commercially available cameras. The image acquisition device may take still images, or it could be a video recording device (such as a camcorder) or any other image acquisition device. Stereo imaging devices are currently preferred, but it is not necessary to have stereo imaging and the present invention is not so limited. Likewise, although it is preferred that the image acquisition device be a digital device, it is not necessary. For example, the image acquisition device could be an analog TV camera that acquires an initial image which is then processed into a digital image for further use in the method of the present invention. The image processor used in the above system may comprise any device programmed and configured to perform the method of counting (and, optionally, classifying) a FU according to the present invention. By way of example, and not limitation, a suitable image processor may be any type of personal computer ("PC"). Alternatively, the image processor may comprise an Application Specific Integrated Circuit (ASIC) or Field Programmable Gate Array (FPGA). In one exemplary embodiment, a system for counting follicular units (FUs) comprises: an image acquisition device and an image processor configured for filtering the image comprising skin and FUs obtained from the image acquisition device to remove background components; processing the image to produce a segmented image; and performing noise filtering of the segmented image to remove objects that do not correspond to FUs of interest.

According to another aspect of the present invention, an image processor for counting follicular units is provided. It may comprise any appropriate device as described above. The image processor may be programmed with software configured to perform the method of counting (and, optionally, classifying) follicular units. In one exemplary embodiment, an image processor for counting follicular units is configured for receiving an image of a body surface comprising skin and follicular units, filtering the image to remove background components, processing the image to produce a segmented image, and performing noise filtering to remove objects that do not correspond to follicular units of interest. Such image processor according to the present invention could be provided separately and used in conjunction with planning of hair treatments, or with various systems for harvesting and/or implanting follicular units (manual, semiautomatic, automatic, or robotic), as well as with various systems for counting or classifying follicular units; alternatively, it could be incorporated in any of the above systems and devices.

The image acquisition device may be provided independently, or it may be mounted in a fixed position, or it may be mounted to a robotic arm or other controllable motion device. The robotic arm or motion device may be operatively coupled to a controller configured to control the motion of the robotic arm or motion device. The controller may receive and process images or data from the image processor with the controller configured to control the motion of the robotic arm or motion device based on the images or data acquired by the image acquisition device. In addition, the system may comprise a hair harvesting and/or implantation tools.

Any of the systems and methods for counting (and classifying) a follicular unit as described herein may be used in conjunction with the system and method of harvesting and transplanting hair as described in U.S. patent application Ser. No. 11/380,903 and U.S. patent application Ser. No. 11/380,907.

The foregoing illustrated and described embodiments of the invention are susceptible to various modifications and alternative forms, and it should be understood that the invention generally, as well as the specific embodiments described herein, are not limited to the particular forms or methods disclosed, but to the contrary cover all modifications, equivalents and alternatives falling within the scope of the appended claims. By way of non-limiting example, it will be appreciated by those skilled in the art that the invention is not limited to the use of a robotic system including a robotic arm, and that other automated and semi-automated systems may be utilized. Moreover, the system and method of counting follicular units of the present invention can be a separate system used along with a separate automated transplantation system or even with a manual transplantation procedure.

The invention claimed is:

1. A method of counting individual follicular units (FUs), comprising:
   filtering an image of a body surface comprising skin and FUs to remove background components;
   processing the image to produce a segmented image;
   performing noise filtering of the segmented image to remove objects having characteristics that do not correspond to individual FUs of interest; and
   counting the individual FUs of interest.

2. The method of claim 1, wherein filtering to remove background components is accomplished using a background subtraction technique.

3. The method of claim 2, wherein the background subtraction technique comprises a variance filtering or an edge detection based process.

4. The method of claim 1, wherein the background subtraction technique comprises computing a blurred image and subtracting the blurred image from the image of a body surface comprising skin and FUs.

5. The method of claim 4, wherein the blurred image is computed by convolving the image of a body surface comprising skin and FUs with a Gaussian kernel.

6. The method of claim 5, wherein the Gaussian kernel is tuned for one or more of:
   a particular patient,
   an ambient lighting condition, and
   other clinical condition.

7. The method of claim 1, wherein filtering to remove background components is accomplished using a band-pass filter.

8. The method of claim 1, wherein filtering to remove background components comprises removing components corresponding to the skin and other small objects from the acquired image.

9. The method of claim 1, wherein filtering to remove background components comprises low-pass filtering a selected image twice and then subtracting the two resulting filtered images from the image of a body surface comprising skin and FUs.

10. The method of claim 1, wherein filtering to remove background components comprises a first filter step in which the image is filtered using a low-pass filter having a first kernel, and a second filter step in which the image is filtered using a low-pass filter having a second kernel.

11. The method of claim 10, wherein the first kernel is a Gaussian kernel having substantially the following characteristics: support 21 pixels and sigma of 1.0, or support 21 pixels and sigma of 0.75.

12. The method of claim 10, wherein the first kernel is different from the second kernel.

13. The method of claim 1, further comprising:
   acquiring at least one additional image of a same field of view at a known position different from a vantage point of the first image of a body surface comprising skin and FUs, wherein the first image and the at least one additional image are acquired in sequence;
   computing the coordinate position of a hair on the body surface using the first and the at least one additional images; and
   filtering out follicular units having a computed coordinate position which is inconsistent with a hair on the body surface.

14. The method of claim 1, wherein noise filtering comprises filtering out any object having an area that differs from a mean object size within the image of a body surface comprising skin and FUs.

15. The method of claim 1, wherein noise filtering comprises filtering out objects whose characteristics include one or more of area, length, location and orientation.

16. The method of claim 1, wherein noise filtering comprises filtering out objects whose characteristics do not correspond to one or more of characteristics for hair based on a sampling of hairs on the body surface and characteristics expected for hair based on predetermined data.

17. The method of claim 1, further comprising tracking an individual FU being counted by:
    acquiring a plurality of images of the individual FU in sequence;
    determining positions of the individual FU from each of the plurality of images; and
    tracking movement of the individual FU based upon the determined positions.

18. The method of claim 1, further comprising classifying an individual FU based on a number of hairs in the individual FU.

19. The method of claim 18, wherein the individual FUs of interest are counted based at least in part upon results of classifying one or more individual FUs to account for any multiple FUs that appear to be a single FU, and/or any single FUs that appear to be multiple FUs.

20. The system of claim 1, wherein the image processor is programmed for classifying individual FUs based on a number of hairs in them.

21. A system for counting individual follicular units (FUs) on a body surface, comprising:
    an interface adapted to receive image data containing FUs; and
    an image processor comprising instructions for
        filtering an image comprising skin and FUs to remove background components;
        processing the image to produce a segmented image;
        performing noise filtering of the segmented image to remove objects having characteristics that do not correspond to individual FUs of interest; and
        counting the individual FUs of interest.

22. The system of claim 21, wherein the system is a robotic system comprising a robotic arm and an image acquisition device.

23. The system of claim 22, further comprising a controller operatively coupled to the robotic arm and the image processor.

24. The system of claim 21, further comprising one or more cameras.

* * * * *